(12) United States Patent
Han et al.

(10) Patent No.: US 9,766,283 B2
(45) Date of Patent: Sep. 19, 2017

(54) TRANSFORMER FAULT DETECTION APPARATUS AND METHOD

(71) Applicant: Korea Electric Power Corporation, Gangnam-gu, Seoul (KR)

(72) Inventors: Kison Han, Daejeon (KR); Jinyul Yoon, Daejeon (KR); Hyungjun Ju, Daejeon (KR); Kijung Ann, Seoul (KR)

(73) Assignee: KOREA ELECTRIC POWER CORPORATION, Gangnam-Gu, Seoul (KR)

( * ) Notice: Subject to any disclaimer, the term of this patent is extended or adjusted under 35 U.S.C. 154(b) by 472 days.

(21) Appl. No.: 14/458,055

(22) Filed: Aug. 12, 2014

(65) Prior Publication Data
US 2015/0091598 A1 Apr. 2, 2015

(30) Foreign Application Priority Data
Sep. 30, 2013 (KR) .................. 10-2013-0116793

(51) Int. Cl.
*G01R 31/08* (2006.01)
*G01R 31/02* (2006.01)
(Continued)

(52) U.S. Cl.
CPC ........... *G01R 31/027* (2013.01); *G01N 29/07* (2013.01); *G01R 31/1227* (2013.01); *G01N 2291/2697* (2013.01); *G01R 31/1209* (2013.01)

(58) Field of Classification Search
CPC .............. G01R 31/027; G01R 31/1209; G01R 31/1227; G01R 31/1254; G01R 31/1272;
(Continued)

(56) References Cited

U.S. PATENT DOCUMENTS 6,774,639 B1\* 8/2004 Unsworth .............. H01H 33/26
324/535
2003/0201780 A1\* 10/2003 Blades ..................... G01R 1/07
324/523
(Continued)

FOREIGN PATENT DOCUMENTS

KR 10-2013-0034774 A 4/2013
WO 94-28566 A1 12/1994

OTHER PUBLICATIONS

Combined Search and Examination Report issued in UK Application No. GB1414814.2, dated Feb. 9, 2015.

*Primary Examiner* — Alesa Allgood
(74) *Attorney, Agent, or Firm* — McDermott Will & Emery LLP

(57) ABSTRACT

The transformer fault detection apparatus includes an integrated sensor unit for sensing signals through a plurality of sensors located on each of upper and lower drain valves in a transformer. A first possible discharge area calculation unit calculates a first possible discharge area estimated to be a location of a partial discharge source of the transformer, based on arrival times of signals sensed by different sensors located on the upper drain valve. A second possible discharge area calculation unit calculates a second possible discharge area estimated to be the location of the partial discharge source, based on arrival times of signals sensed by different sensors located on the lower drain valve. A final possible discharge area calculation unit calculates a final possible discharge area, based on an overlapping area between the first and second possible discharge areas.

12 Claims, 10 Drawing Sheets

(51) Int. Cl.
*G01N 29/07* (2006.01)
*G01R 31/12* (2006.01)

(58) Field of Classification Search
CPC .... G01R 31/14; G01R 31/16; G01N 33/2841; B01D 19/0031
See application file for complete search history.

(56) References Cited

U.S. PATENT DOCUMENTS

2005/0086998 A1* 4/2005 Qin .................... B01D 19/0031 73/31.07
2010/0240999 A1* 9/2010 Droitcour ................ A61B 5/05 600/453

* cited by examiner

TRANSFORMER FAULT DETECTION APPARATUS AND METHOD

CROSS REFERENCE TO RELATED APPLICATION

This application claims the benefit of Korean Patent Application No. 10-2013-0116793, filed Sep. 30, 2013, which is hereby incorporated by reference in its entirety into this application.

BACKGROUND OF THE INVENTION

1. Technical Field

The present invention relates generally to a transformer fault detection apparatus and method. More particularly, the present invention relates to a transformer fault detection apparatus and method, in which a plurality of sensors are integrally mounted on a drain valve in the transformer, and which estimate the location of a partial discharge source in the transformer based on different signals sensed by the sensors.

2. Description of the Related Art

In order to detect an abnormal signal occurring due to the internal fault of a transformer, a scheme for installing an ultrasonic sensor on the enclosure of the transformer and measuring an abnormal signal, a scheme for installing an insertion-type Ultra High Frequency (UHF) electromagnetic sensor in the drain valve of the transformer and acquiring an abnormal signal, or a scheme for filling the inside of the transformer with insulating oil and remotely and periodically analyzing a dissolved gas, has been used, wherein a gas analysis device capable of detecting hydrogen or moisture is applied to some transformers.

In this case, when the ultrasonic sensor is attached to the enclosure of the transformer, there is a problem in that external noise from a power device in operation flows into the transformer, and thus it is difficult to identify a partial discharge signal. The UHF electromagnetic sensor to be inserted into the drain valve is disadvantageous in that sensors are required to be installed at two places, that is, the upper valve and the lower valve of the transformer, thus making it impossible to estimate the precise location of an abnormal signal. Further, the scheme for filling the inside of the transformer with insulating oil and analyzing a dissolved gas is disadvantageous in that it is impossible to monitor the internal abnormality of the transformer in real time, and some online gas analysis devices are foreign devices, and are thus expensive and difficult to maintain.

In particular, the detection of internal faults of the transformer using ultrasonic waves is configured such that when a partial discharge occurs in the transformer, surrounding insulating oil is suddenly compressed due to local heat generation around the partial discharge, and the location at which an abnormality has occurred can be estimated using a scheme for measuring pulse-shaped sound waves and ultrasonic waves occurring when shock waves attributable to such compression are transferred to the oil. However, there is a disadvantage in that it is impossible to measure the charge quantity of the partial discharge, and in that a precise correction of an estimated location is required due to the inflow of noise signals, such as external vibration or wind. Further, there is a fatal disadvantage in that it is difficult to distinguish a partial discharge signal caused by the internal defect of the transformer from an external noise signal, and thus such a scheme is still in a testing stage.

FIG. 1 is a diagram showing a method of detecting an internal defect of a conventional transformer.

In detail, when conventional technology is described with reference to FIG. 1, ultrasonic analysis equipment a, electromagnetic partial discharge analysis equipment b, and online gas analysis equipment c are located on a transformer T. In this case, since separate sensor devices are required to be installed depending on respective diagnosis schemes, the attachment, detachment, and maintenance of sensors is difficult, and each individual sensor is expensive, thus causing the problems of deteriorated diagnosis reliability and insufficient economic efficiency.

Therefore, there is required a transformer fault detection apparatus and method that can precisely estimate the location of a partial discharge source in a transformer by integrally mounting a plurality of sensors on a drain valve in the transformer and then sensing signals. As technology related to the present invention, there is Korean Patent Application Publication No. 2013-0034774.

SUMMARY OF THE INVENTION

Accordingly, the present invention has been made keeping in mind the above problems occurring in the prior art, and an object of the present invention is to precisely and easily measure an abnormal signal such as a partial discharge signal in a transformer by installing sensors, which simultaneously measure an electromagnetic signal and an ultrasonic signal occurring in the transformer, on the drain valve of the transformer in order to detect a partial discharge and an arc occurring in the transformer.

Another object of the present invention is to sense signals using an integrated sensor unit installed on upper and lower drain valves present in the transformer and to precisely estimate the location of a partial discharge occurring in the transformer using a difference between the propagation velocity of an electromagnetic signal and the propagation velocity of an ultrasonic signal within the insulating oil.

In accordance with an aspect of the preset invention to accomplish the above objects, there is provided a transformer fault detection apparatus, including an integrated sensor unit for sensing signals through a plurality of sensors located on each of an upper drain valve and a lower drain valve present in a transformer, a first possible discharge area calculation unit for calculating a first possible discharge area estimated to be a location of a partial discharge source of the transformer, based on arrival times of signals sensed by different sensors located on the upper drain valve, a second possible discharge area calculation unit for calculating a second possible discharge area estimated to be the location of the partial discharge source of the transformer, based on arrival times of signals sensed by different sensors located on the lower drain valve, and a final possible discharge area calculation unit for calculating a final possible discharge area estimated to be the location of the partial discharge source of the transformer, based on an overlapping area between the first possible discharge area and the second possible discharge area.

The transformer fault detection apparatus may further include a possible discharge area correction unit for correcting the first possible discharge area and the second possible discharge area based on media of the signals.

The transformer fault detection apparatus may further include a partial discharge source location estimation unit for estimating the location of the partial discharge source from the final possible discharge area, based on a difference between arrival times of an identical signal that has reached a sensor located on the upper drain valve and a sensor located on the lower drain valve.

The integrated sensor unit may include at least one ultrasonic sensor and at least one electromagnetic sensor, wherein the ultrasonic sensor and the electromagnetic sensor are integrally coupled to each other.

The first possible discharge area calculation unit may calculate a three-dimensional (3D) first possible discharge area, based on a difference between arrival times of a first electromagnetic signal sensed by a first electromagnetic sensor located on the upper drain valve and a first ultrasonic signal sensed by a first ultrasonic sensor located on the upper drain valve.

The second possible discharge area calculation unit may calculate a 3D second possible discharge area, based on a difference between arrival times of a second electromagnetic signal sensed by a second electromagnetic sensor located on the lower drain valve and a second ultrasonic signal sensed by a second ultrasonic sensor located on the lower drain valve.

The final possible discharge area calculation unit may calculate a two-dimensional (2D) final possible discharge area generated by causing a point, at which the 3D first possible discharge area and the 3D second possible discharge area intersect each other, to be included in a circumference.

The partial discharge source location estimation unit may estimate the location of the partial discharge source from the final possible discharge area, based on a difference between arrival times of the first electromagnetic signal and the second electromagnetic signal.

The integrated sensor unit may further include a gas sensor located on the upper drain valve or the lower drain valve and configured to sense gas contained in insulating oil present in the transformer while being in direct contact with the insulating oil.

The integrated sensor unit may further include a temperature sensor located on the upper drain valve or the lower drain valve and configured to sense a temperature of the insulating oil present in the transformer.

In accordance with another aspect of the preset invention to accomplish the above objects, there is provided a transformer fault detection method, including calculating, by a first possible discharge area calculation unit, a first possible discharge area estimated to be a location of a partial discharge source of a transformer, based on arrival times of signals sensed by different sensors located on an upper drain valve present in an upper portion of the transformer, calculating, by a second possible discharge area calculation unit, a second possible discharge area estimated to be the location of the partial discharge source of the transformer, based on arrival times of signals sensed by different sensors located on a lower drain valve present in a lower portion of the transformer, and calculating, by a final possible discharge area calculation unit, a final possible discharge area estimated to be the location of the partial discharge source of the transformer, based on an overlapping area between the first possible discharge area and the second possible discharge area.

The transformer fault detection method may further include correcting the first possible discharge area and the second possible discharge area based on media of the signals.

The transformer fault detection method may further include, after calculating the final possible discharge area, estimating the location of the partial discharge source from the final possible discharge area, based on a difference between arrival times of an identical signal that has reached a sensor located on the upper drain valve and a sensor located on the lower drain valve.

The upper drain valve and the lower drain valve may be configured such that an ultrasonic sensor and an electromagnetic sensor are located on each of the upper drain valve and the lower drain valve, the ultrasonic sensor and the electromagnetic sensor being integrally coupled to each other.

Calculating the first possible discharge area may include calculating a three-dimensional (3D) first possible discharge area, based on a difference between arrival times of a first electromagnetic signal sensed by a first electromagnetic sensor located on the upper drain valve and a first ultrasonic signal sensed by a first ultrasonic sensor located on the upper drain valve.

Calculating the second possible discharge area may include calculating a 3D second possible discharge area, based on a difference between arrival times of a second electromagnetic signal sensed by a second electromagnetic sensor located on the lower drain valve and a second ultrasonic signal sensed by a second ultrasonic sensor located on the lower drain valve.

Calculating the final possible discharge area may include calculating a two-dimensional (2D) final possible discharge area generated by causing a point, at which the 3D first possible discharge area and the 3D second possible discharge area intersect each other, to be included in a circumference.

Estimating the location of the partial discharge source may include estimating the location of the partial discharge source from the final possible discharge area, based on a difference between arrival times of the first electromagnetic signal and the second electromagnetic signal.

The transformer fault detection method may further include sensing gas contained in insulating oil present in the transformer through a gas sensor located on the upper drain valve or the lower drain valve and configured to be in direct contact with the insulating oil.

The transformer fault detection method may further include sensing a temperature of insulating oil present in the transformer through a temperature sensor located on the upper drain valve or the lower drain valve.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
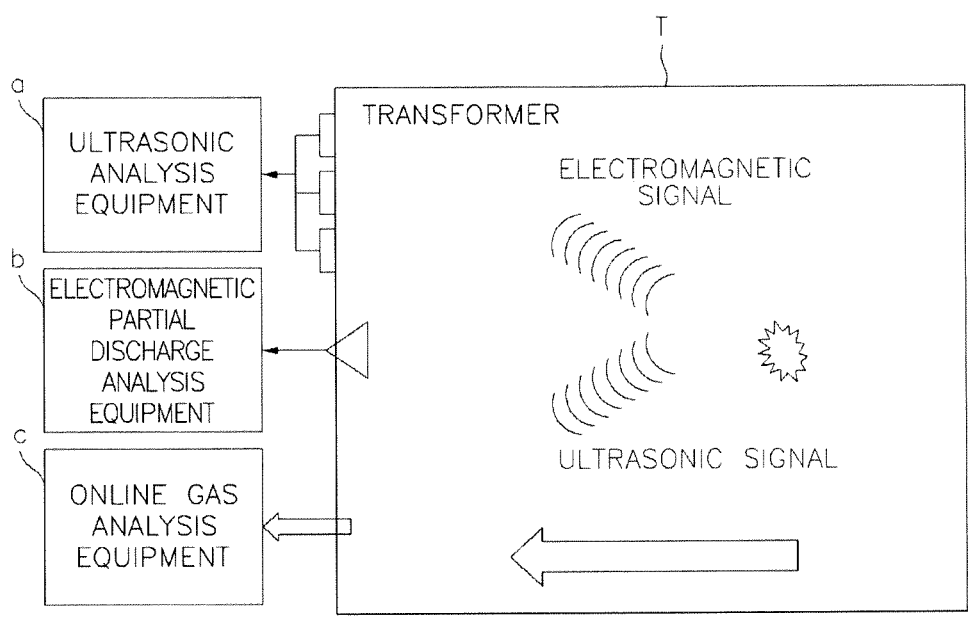
FIG. 1 is a diagram showing a conventional method of detecting the internal fault of a transformer.

The present invention will be described in detail below with reference to the accompanying drawings. Repeated descriptions and descriptions of known functions and configurations which have been deemed to make the gist of the present invention unnecessarily obscure will be omitted below.

The embodiments of the present invention are intended to fully describe the present invention to a person having ordinary knowledge in the art to which the present invention pertains.

Accordingly, the shapes, sizes, etc. of components in the drawings may be exaggerated to make the description clearer.

Hereinafter, an example of a configuration that may be implemented when a transformer fault detection apparatus according to the present invention is employed will be described in brief.

Figure 2:
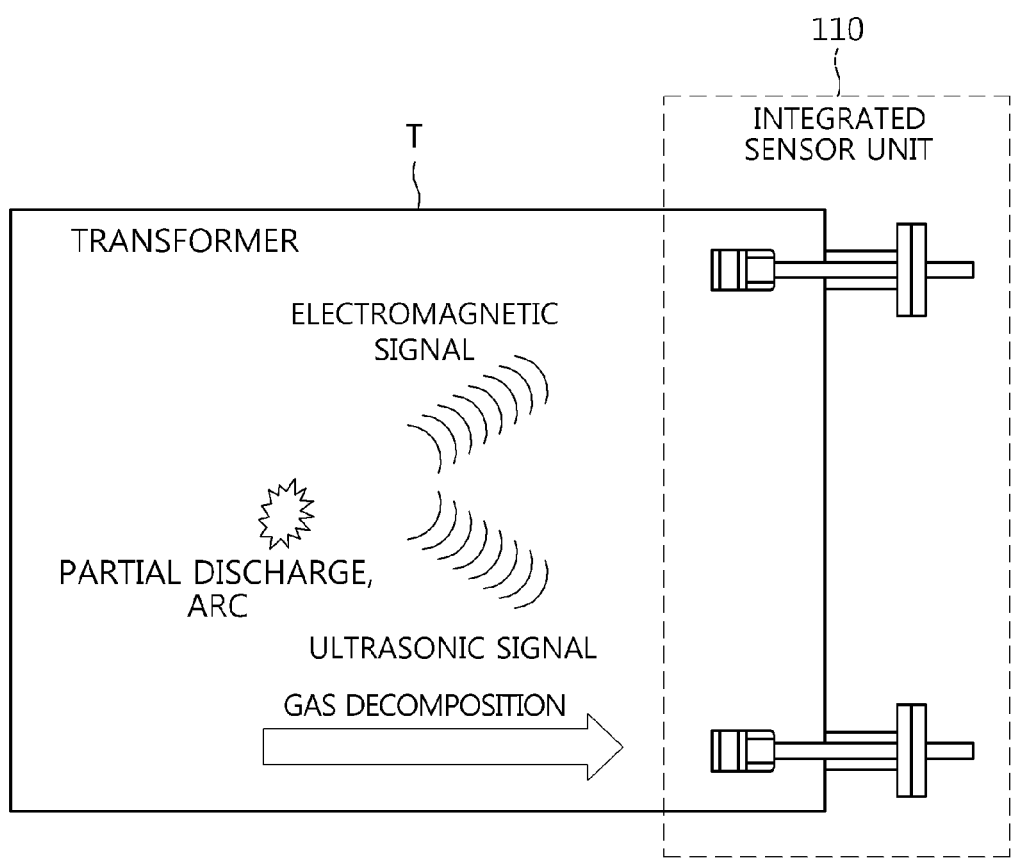
FIG. 2 is a diagram showing the sensor of a transformer fault detection apparatus according to the present invention.

FIG. 2 is a diagram showing the sensor of a transformer fault detection apparatus according to the present invention.

Figure 3:
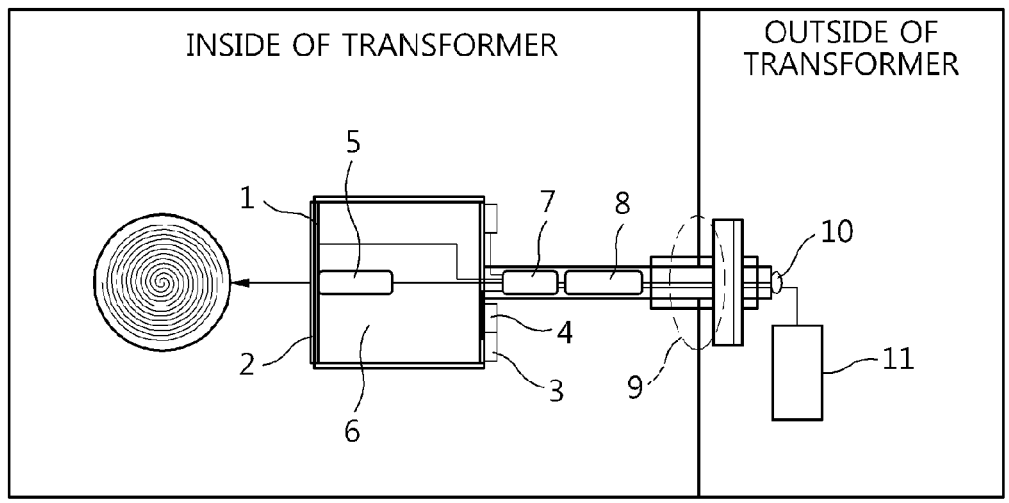
FIG. 3 is a diagram showing the concept of the configuration of a transformer fault detection apparatus according to the present invention.

When a description is made with reference to FIGS. 2 and 3 together, the transformer fault detection apparatus according to the present invention employs an improved measurement method. FIG. 3 is a diagram showing the concept of the configuration of a transformer fault detection apparatus according to the present invention.

In detail, an integrated sensor unit 110 is provided which includes a plurality of sensors on each of an upper drain valve and a lower drain valve present in a transformer T.

As described above, in accordance with conventional technology, each sensor is separately designed, and an ultrasonic wave, an electromagnetic wave, etc. are sensed by respective sensors, whereas the present invention employs an integrated sensor unit in which a plurality of sensors are integrally coupled to each of the upper drain valve and the lower drain valve.

Referring to FIG. 3, an embodiment of the design according to the present invention will be described. A transformer T includes therein an ultrasonic sensor 1, an electromagnetic sensor 2, a gas sensor 3, a temperature sensor 4, an ultrasonic sensor piezoelectric ceramic (lead zirconate titanate: PZT) 5, a damper (filler) 6, an amplifier 7, a data measurement unit 8, and a drain valve 9. Further, a signal output unit 10 and a power unit 11 are located outside the transformer T.

The ultrasonic sensor 1 has the function of measuring an ultrasonic signal occurring in the transformer T, and may be configured to be integrated with the electromagnetic sensor 2.

In detail, the ultrasonic sensor 1 may be configured to be installed in the transformer T via the drain valve 9 rather than a scheme vulnerable to noise in such a way that it is installed in the enclosure of a power transformer T as in an existing scheme.

Further, the ultrasonic sensor 1 shares a receiving plate for acquiring an ultrasonic signal with the electromagnetic sensor 2, so that the electromagnetic sensor 2 and the ultrasonic sensor 1 are manufactured in a single board, thus realizing the small size and light weight of the device. Further, an ultrasonic signal is obtained using the piezoelectric ceramic 5 on the receiving plate.

Furthermore, wideband response characteristics are obtained using the filler 6 in the ultrasonic sensor 1, and the measured ultrasonic signal is amplified via the amplifier 7 and then transferred to the data measurement unit 8. By shortening the distance between the ultrasonic sensor 1 and the amplifier 7, the measured ultrasonic signal is robust to external noise, and is transferred without signal attenuation.

Furthermore, the receiving plate of the ultrasonic sensor 1 and the support plate of the electromagnetic sensor 2 are manufactured as a single identical thin plate made of a ceramic material. On the plate made of the ceramic material, the electromagnetic sensor 2 is installed using metal such as copper to obtain electromagnetic signals. Since the sensitivity of the electromagnetic sensor 2 is determined depending on a distance d between the sensor and a ground plate, and the dielectric constant of the filler 6 between the sensor and the ground plate, the plate used both as the support plate of the electromagnetic sensor 2 and the receiving plate of the ultrasonic sensor 1 may be configured to have the same dielectric constant as the filler.

Further, when the ultrasonic signal is transferred to the receiving plate, it is transferred to the piezoelectric ceramic located on the rear side of the receiving plate. In this case, since the intensity of the transferred signal varies with the strength of the receiving plate, the receiving plate is configured such that it is made of a ceramic material having excellent strength and the dielectric constant thereof at this time is identical to that of the filler 6.

That is, in a conventional ultrasonic sensor attached to the enclosure of the transformer T, it is difficult to perform measurement due to the inflow of noise attributable to external vibration or the like because ultrasonic waves, generated due to the partial discharge of the transformer and transferred to a tank through insulating oil, are detected by an Acoustic Emission (AE) sensor attached to the enclosure of the transformer. In contrast, the present invention is characterized in that it directly measures ultrasonic waves, transferred through insulating oil, by using the ultrasonic sensor 1 installed on the drain valve 9 of the transformer T without measuring ultrasonic waves transferred to the enclosure of the transformer T, thus remarkably reducing the distortion, velocity difference, attenuation, and external vibration noise of ultrasonic signals transferred along the enclosure.

The electromagnetic sensor 2 is located in the transformer T after passing through the drain valve 9 of the transformer T and has the function of detecting a partial discharge signal generated in the transformer T.

In detail, the electromagnetic sensor 2 is configured to be installed in the power transformer T through the drain valve 9 of the transformer T, and the sensitivity of the electromagnetic sensor 2 is determined depending on a distance between the electromagnetic sensor unit and the ground plate of a patch antenna manufactured in a spiral shape, and the relative dielectric constant of the internal filler 6. Therefore, the electromagnetic sensor 2 is manufactured by adjusting the diameter of the drain valve 9, a distance between the sensor and the ground plate, and the relative dielectric constant of the filler 6 so that the resonance point of the sensor is present in a 500 MHz~1,500 MHz frequency band which is the electromagnetic frequency band of the transformer T. Further, the electromagnetic sensor 2 may be configured to transmit voltages between the sensor units and the ground plates of patch antennas manufactured in various shapes to the data measurement unit 8 through a amplifier.

Further, the antenna of the electromagnetic sensor 2 is configured to have the shape of any of a circular dipole patch antenna, a planar log-periodic patch antenna, a spiral patch antenna, and an Archimedes patch antenna.

The gas sensor 3 may be located in a shape that comes into direct contact with the insulating oil in the transformer T after passing through the drain valve 9 of the transformer T, and may measure hydrogen and carbon-based gases contained in the insulating oil.

In detail, the gas sensor 3 may be composed of a palladium-nickel (pd—ni) sensor for measuring a hydrogen gas and a Carbon Nano Tube (CNT) sensor for measuring Total Combustible Gas (TCG) using the CNT.

Further, the gas sensor 3 is configured to be attached to the ground plate of the integrated sensor unit 110 and to transfer a measured signal to the data measurement unit 8 through the amplifier 7.

The temperature sensor 4 has the function of measuring the temperature of the insulating oil in the transformer T, and is configured as a structure capable of having a maximum area on the ground plate so that the temperature sensor 4 does not cause interference with the electromagnetic sensor 2 and the ultrasonic sensor 1.

In detail, the temperature sensor 4 is attached to the ground plate of the integrated sensor unit 110 and is configured to directly measure the temperature of the insulating oil of the power transformer T and to transfer the measured temperature to the data measurement unit 8 through the amplifier 7.

The signal output unit 10 functions to transfer the signals measured by the electromagnetic sensor 2, the ultrasonic sensor 1, the gas sensor 3, and the temperature sensor 4 to the outside of the transformer, and is configured to allow the transferred signals to be applied to measurement equipment and the signals of the respective sensors to be analyzed.

The power unit 11 functions to supply power to the electromagnetic sensor 2, the ultrasonic sensor 1, the gas sensor 3, and the temperature sensor 4, and is configured to allow the supplied power to be used as the power of the amplifier of each sensor, prevent sensor signals depending on the transfer distance from being attenuated, and allow the data measurement unit 8 for measuring signals to have optimal sensitivity.

As described above, the present invention functions to measure signals acquired through the sensors in connection with external measurement equipment via the signal output unit 10 and implements the signal output unit 10 as a connector such as an n-type or a Bayonet Neill-Concelman (BNC)-type connector. Then, the present invention is designed to have a structure capable of minimizing the disturbance of measured signals attributable to external noise by receiving power from the outside through the connector to operate the amplifier 7.

Hereinafter, the configuration and operating principle of the transformer fault detection apparatus according to the present invention will be described in detail.

Figure 4:
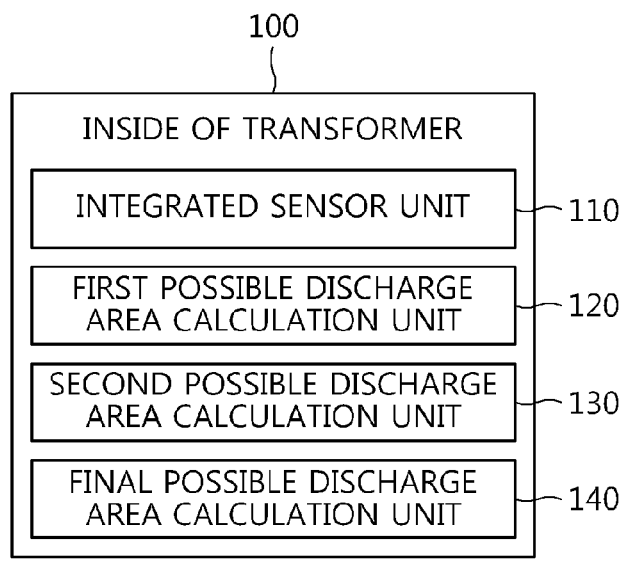
FIG. 4 is a block diagram showing a transformer fault detection apparatus according to the present invention.
Figure 5:
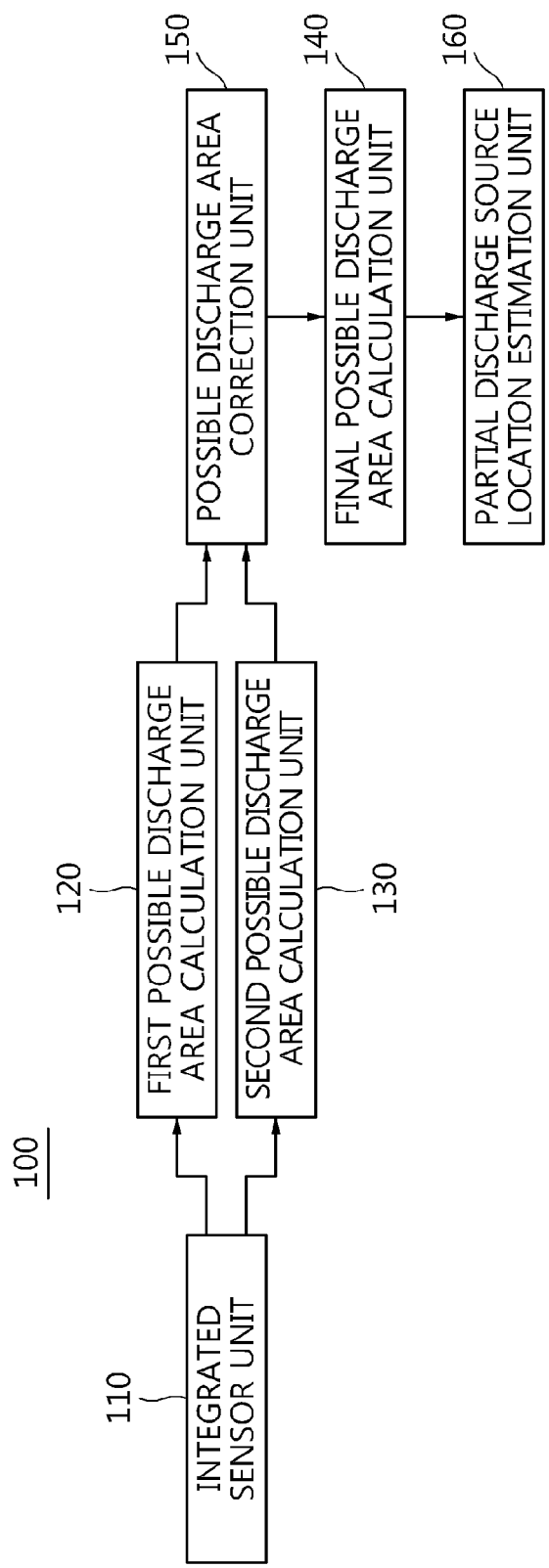
FIG. 5 is a diagram showing an embodiment of the transformer fault detection apparatus according to the present invention.

FIG. 4 is a block diagram showing a transformer fault detection apparatus. FIG. 5 is a diagram showing an embodiment of the transformer fault detection apparatus according to the present invention.

When a description is made with reference to FIGS. 4 and 5, a transformer fault detection apparatus 100 according to the present invention includes an integrated sensor unit 110, a first possible discharge area calculation unit 120, a second possible discharge area calculation unit 130, and a final possible discharge area calculation unit 140. The integrated sensor unit 110 senses signals through a plurality of sensors located on each of an upper drain valve and a lower drain valve present in a transformer. The first possible discharge area calculation unit 120 calculates a first possible discharge area estimated to be the location of the partial discharge source of the transformer, based on the arrival times of signals sensed by different sensors located on the upper drain valve. The second possible discharge area calculation unit 130 calculates a second possible discharge area estimated to be the location of the partial discharge source of the transformer, based on the arrival times of signals sensed by different sensors located on the lower drain valve. The final possible discharge area calculation unit 140 calculates a final possible discharge area estimated to be the location of the partial discharge source of the transformer, based on an overlapping area between the first possible discharge area and the second possible discharge area.

In this case, the transformer fault detection apparatus 100 according to the present invention may further include a possible discharge area correction unit 150 for correcting the first possible discharge area and the second possible discharge area based on the media of the signals.

The transformer fault detection apparatus 100 may further include a partial discharge source location estimation unit 160 for estimating the location of the partial discharge source from the final possible discharge area, based on a difference between the arrival times of an identical signal that reached a sensor located on the upper drain valve and a sensor located on the lower drain valve.

The integrated sensor unit 110 functions to sense signals through the plurality of sensors located on each of the upper drain valve and the lower drain valve present in the transformer.

In detail, the integrated sensor unit 110 includes an ultrasonic sensor and an electromagnetic sensor, which may be integrally coupled to each other.

In greater detail, the upper drain valve and the lower drain valve are present in the transformer and are each connected to a plurality of sensors. In this case, the plurality of sensors may be an ultrasonic sensor and an electromagnetic sensor.

For example, a single ultrasonic sensor and a single electromagnetic sensor may be coupled to the upper drain valve. Similarly, a single ultrasonic sensor and a single electromagnetic sensor may be coupled to the lower drain valve.

In this case, the integrated sensor unit 110 may include a gas sensor and a temperature sensor as well as the ultrasonic sensors and the electromagnetic sensors.

The gas sensor is located on the upper drain valve or the lower drain valve, and performs the function of sensing gas contained in insulating oil present in the transformer while being in direct contact with the insulating oil. The temperature sensor is located on the upper drain valve or the lower drain valve, and performs the function of sensing the temperature of the insulating oil present in the transformer.

The first possible discharge area calculation unit 120 functions to calculate the first possible discharge area estimated to be the location of the partial discharge source of the transformer, based on the arrival times of signals sensed by different sensors located on the upper drain valve.

In detail, the first possible discharge area calculation unit 120 functions to, when a fault occurs in the transformer to cause a partial discharge, estimate the location of the source of the partial discharge.

Here, the first possible discharge area denotes the location of the partial discharge source estimated based on the arrival times of the signals sensed by the sensors located on the upper drain valve.

Figure 6:
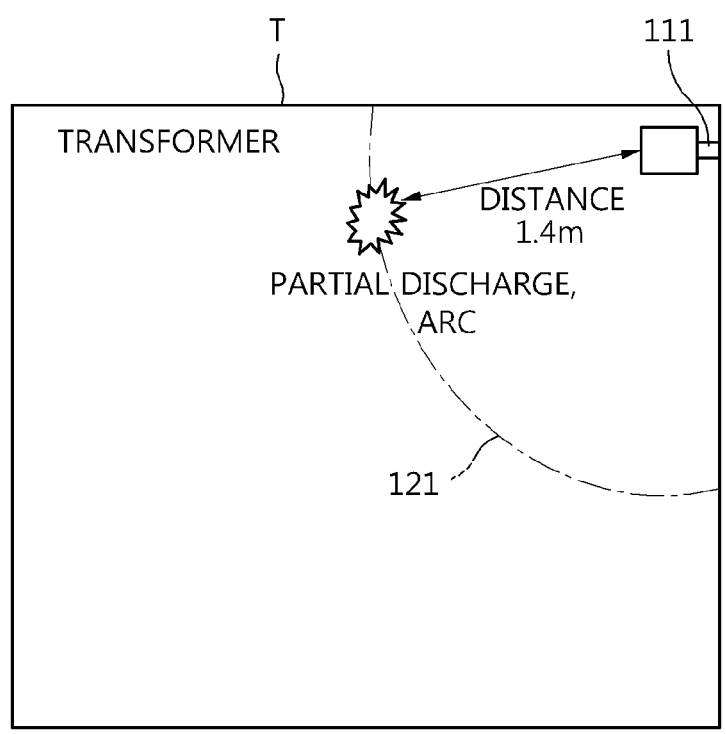
FIG. 6 is a diagram showing a procedure for calculating a first possible discharge area using the transformer fault detection apparatus according to the present invention.

FIG. 6 is a diagram showing a procedure for calculating a first possible discharge area using the transformer fault detection apparatus according to the present invention.

When a description is made in detail with reference to FIG. 6, the first possible discharge area calculation unit 120 may calculate a first possible discharge area based on a difference between the arrival times of a first electromagnetic signal sensed by a first electromagnetic sensor located on the upper drain valve 111 and of a first ultrasonic signal sensed by a first ultrasonic sensor located on the upper drain valve 111.

Referring continuously to FIG. 6, a first possible discharge area 121 has the shape of a three-dimensional (3D) sphere having a radius of 1.4 m around sensors located on the upper drain valve 111 as the center (origin) of the sphere. However, since the location of the partial discharge source is present in the transformer, the outer area of the transformer in the shape of the 3D sphere is not taken into consideration.

That is, the outer area of the transformer is not included the first possible discharge area 121.

As described above, in order to calculate a radius of 1.4 m, a difference between the time at which the first ultrasonic signal has reached the first ultrasonic sensor and the time at which the first electromagnetic signal has reached the first electromagnetic sensor is used.

In order to calculate the first possible discharge area 121, the radius must be calculated. A detailed method for such calculation uses the following Equations (1) and (2):

$$\Delta t = (t2 - t1) = \frac{L}{V2} - \frac{L}{V1} = L\left(\frac{L}{V2} - \frac{L}{V1}\right) \quad (1)$$

In Equation (1), $\Delta t$ denotes a difference between the arrival time of the ultrasonic wave and the arrival time of the electromagnetic wave, t2 denotes the arrival time of the ultrasonic wave, and t1 denotes the arrival time of the electromagnetic wave. Further, V2 denotes the propagation velocity of the ultrasonic wave and V1 denotes the propagation velocity of the electromagnetic wave. Furthermore, L denotes a radius.

Here, V2 is a designated value set to $1.4 \times 10^3$ m/s and V1 is a constant set to a value of $3 \times 10^8$ m/s.

If Equation (1) is arranged for L, it may be represented by the following Equation (2):

$$L = \frac{\Delta t}{\left(\frac{1}{V2} - \frac{1}{V1}\right)} = \frac{\Delta t}{\left(\frac{V1 - V2}{V2V1}\right)} = \Delta t \times \frac{V1V2}{(V1 - V2)} \quad (2)$$

The value of L is calculated by Equation (2), and thus the first possible discharge area 121 can be calculated.

The second possible discharge area calculation unit 130 functions to calculate a second possible discharge area estimated to be the location of the partial discharge source of the transformer, based on the arrival times of the signals sensed by different sensors located on the lower drain valve.

In detail, when a fault occurs in the transformer and a partial discharge occurs, the second possible discharge area calculation unit 130 functions to estimate the location of the partial discharge source.

Here, the second possible discharge area denotes the location of the partial discharge source estimated based on the arrival times of the signals sensed by the sensors located on the lower drain valve.

Figure 7:
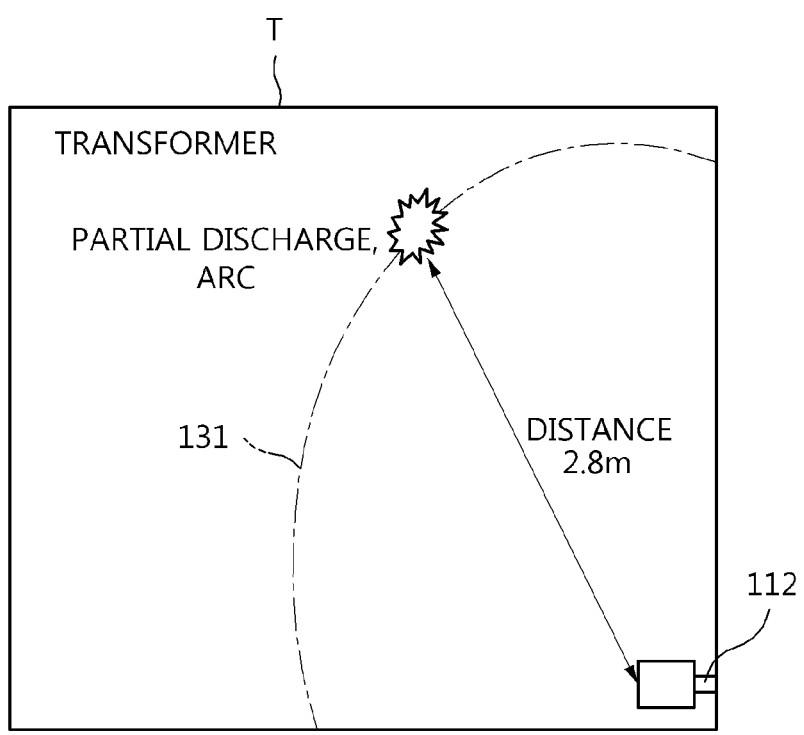
FIG. 7 is a diagram showing a procedure for calculating a second possible discharge area using the transformer fault detection apparatus according to the present invention.

FIG. 7 is a diagram showing a procedure for calculating a second possible discharge area using the transformer fault detection apparatus according to the present invention.

When a description is made in detail with reference to FIG. 7, the second possible discharge area calculation unit 130 may calculate the second possible discharge area based on a difference between the arrival times of a second electromagnetic signal sensed by a second electromagnetic sensor located on a lower drain valve 112 and a second ultrasonic signal sensed by the second ultrasonic sensor located on the lower drain valve 112.

Referring continuously to FIG. 7, a second possible discharge area 131 has the shape of a 3D sphere having a radius of 2.8 m around sensors located on the lower drain valve 112 as the center (origin) of the sphere. However, since the location of the partial discharge source is present in the transformer, the outer area of the transformer in the shape of the 3D sphere is not taken into consideration.

That is, the outer area of the transformer is not included the second possible discharge area 131.

As described above, in order to calculate a radius of 2.8 m, a difference between the time at which the second ultrasonic signal has reached the second ultrasonic sensor and the time at which the second electromagnetic signal has reached the second electromagnetic sensor is used.

In order to calculate the second possible discharge area 131, the radius must be calculated. A detailed method for such calculation uses the above Equations (1) and (2) in the same manner as the method of calculating the first possible discharge area 121.

The possible discharge area correction unit 150 performs the function of correcting the first possible discharge area and the second possible discharge area based on the media of the signals.

Figure 8:
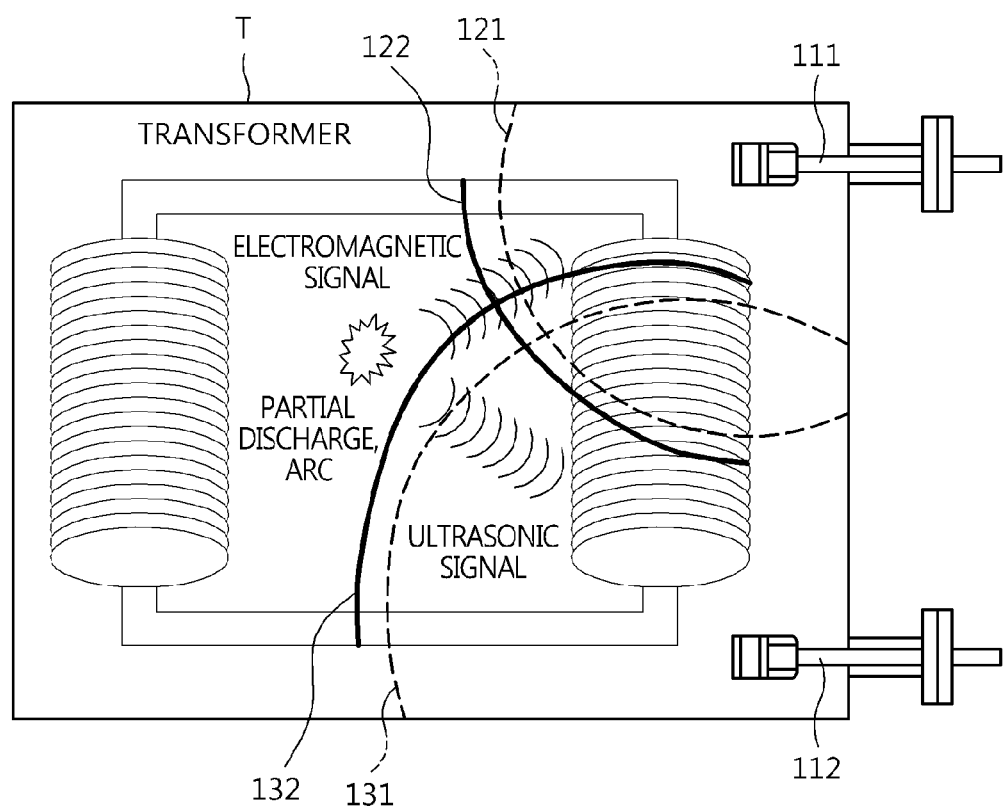
FIG. 8 is a diagram showing the function and operating principle of the possible discharge area correction unit of the transformer fault detection apparatus according to the present invention.

FIG. 8 is a diagram showing the function and operating principle of the possible discharge area correction unit of the transformer fault detection apparatus according to the present invention.

Referring to FIG. 8, after a first possible discharge area 121 formed based on the upper drain valve 111 in a transformer T and a second possible discharge area 131 formed based on the lower drain valve 112 in the transformer T have been calculated, the first possible discharge area 121 is corrected to obtain a corrected first possible discharge area 122, and the second possible discharge area 131 is corrected to obtain a corrected second possible discharge area 132.

In detail, in partial areas of the calculated first and second possible discharge areas 121 and 131, which overlap the iron core of the transformer T, a possible discharge area must be calculated by converting a propagation velocity into the propagation velocity of an ultrasonic signal (3 m/ms) through metal rather than the propagation velocity of an ultrasonic signal through the insulating oil, used in Equations (1) and (2). Similarly, in partial areas of the calculated first and second possible discharge areas 121 and 131, which overlap the coil of the transformer T, a possible discharge area must be calculated by converting a propagation velocity into the average (2.2 m/ms) of the propagation velocity of an ultrasonic signal (3 m/ms) through metal and the propagation velocity of an ultrasonic signal (1.4 m/ms) through the insulating oil, rather than the propagation velocity alone of an ultrasonic signal through the insulating oil, used in Equations (1) and (2).

Therefore, the 3D distances to the insulating oil, the iron core, and the coil, which overlap the first possible discharge area 121 formed based on the upper drain valve 111 in the transformer T or the second possible discharge area 131 formed based on the lower drain valve 112 in the transformer T, are calculated, and the possible discharge areas may be corrected in consideration of the propagation velocities depending on the media using the calculated distances to the insulating oil, the iron core, and the coil.

The final possible discharge area calculation unit 140 functions to calculate the final possible discharge area estimated to be the location of the partial discharge source of the transformer, based on an overlapping area between the first possible discharge area and the second possible discharge area.

The partial discharge source location estimation unit 160 functions to estimate the location of the partial discharge source from the final possible discharge area, based on a difference between the arrival times of the first electromagnetic signal and the second electromagnetic signal.

Figure 9:
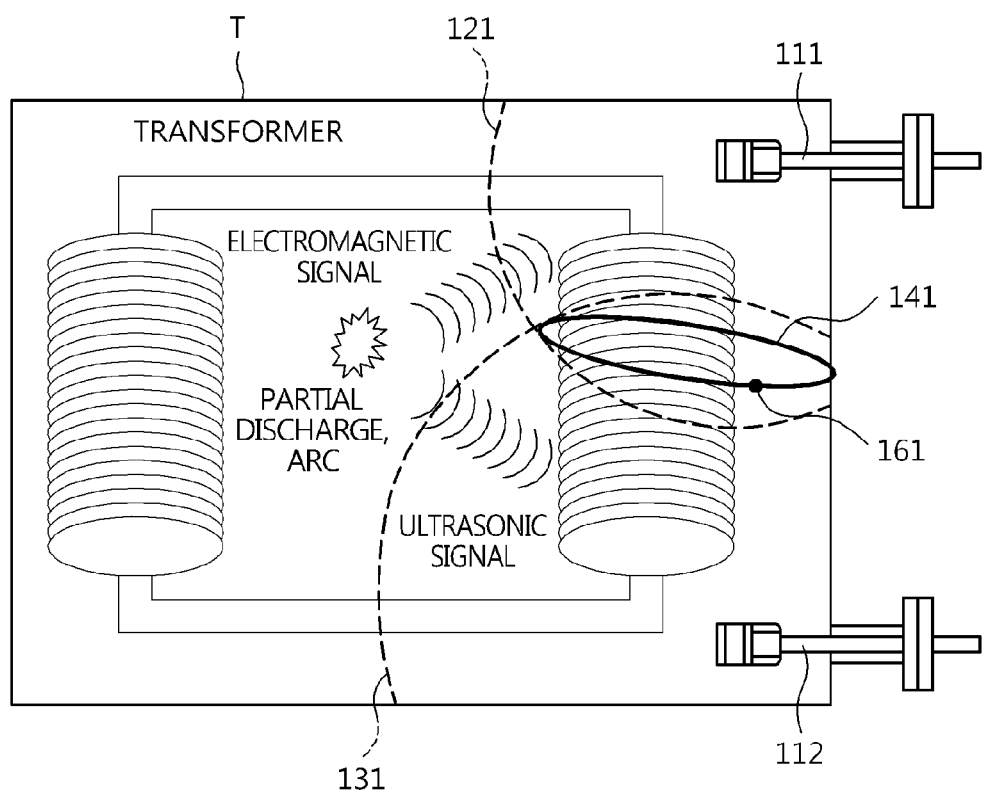
FIG. 9 is a diagram showing a procedure for calculating a final possible discharge area and estimating the location of a partial discharge source using the transformer fault detection apparatus according to the present invention.

FIG. 9 is a diagram showing a procedure for calculating a final possible discharge area and estimating the location of a partial discharge source using the transformer fault detection apparatus according to the present invention.

When a description is made in detail with reference to FIG. 9, the final possible discharge area calculation unit 140 calculates a 2D final possible discharge area 141 by causing a point, at which a 3D first possible discharge area and a 3D second possible discharge area intersect, to be included in a circumference.

Further, the partial discharge source location estimation unit 160 uses a difference between the arrival times of the first electromagnetic signal and the second electromagnetic signal so as to precisely estimate the location of the partial discharge source as a single point in the final possible discharge area 141. The difference between the arrival times of the first electromagnetic signal and the second electromagnetic signal is a value obtained from discharge occurring at one point on the circumference of the final possible discharge area 141. The time differences between individual locations on the circumference and the sensors on the upper/lower drain valves are calculated using the distances between the individual locations on the circumference and the sensors, as given by the following Equation (3), and then a table is generated. After, a point on the circumference at which time differences are coincident with each other based on the table is estimated to be the location 161 of the partial discharge source.

$$\Delta t = V(L1 - L2) \quad (3)$$

In Equation (3), $\Delta t$ denotes the difference between the arrival time of the first electromagnetic signal which is an electromagnetic signal that has reached the sensor mounted on the upper drain valve and the arrival time of the second electromagnetic signal which is an electromagnetic signal that has reached the sensor mounted on the lower drain valve. Further, V denotes the propagation velocity of the electromagnetic signal, L1 denotes a distance from the location of the partial discharge source to the sensor mounted on the upper drain valve, and L2 denotes a distance from the location of the partial discharge source to the sensor mounted on the lower drain valve.

Hereinafter, a transformer fault detection method according to the present invention will be described. In this case, a repeated description of the same components as those of the transformer fault detection apparatus 100 will be omitted.

Figure 10:
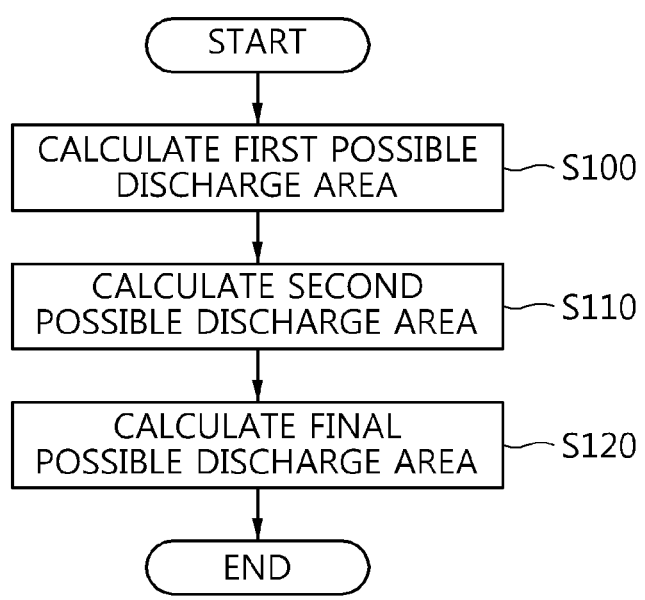
FIG. 10 is a flowchart showing a transformer fault detection method according to the present invention.
Figure 11:
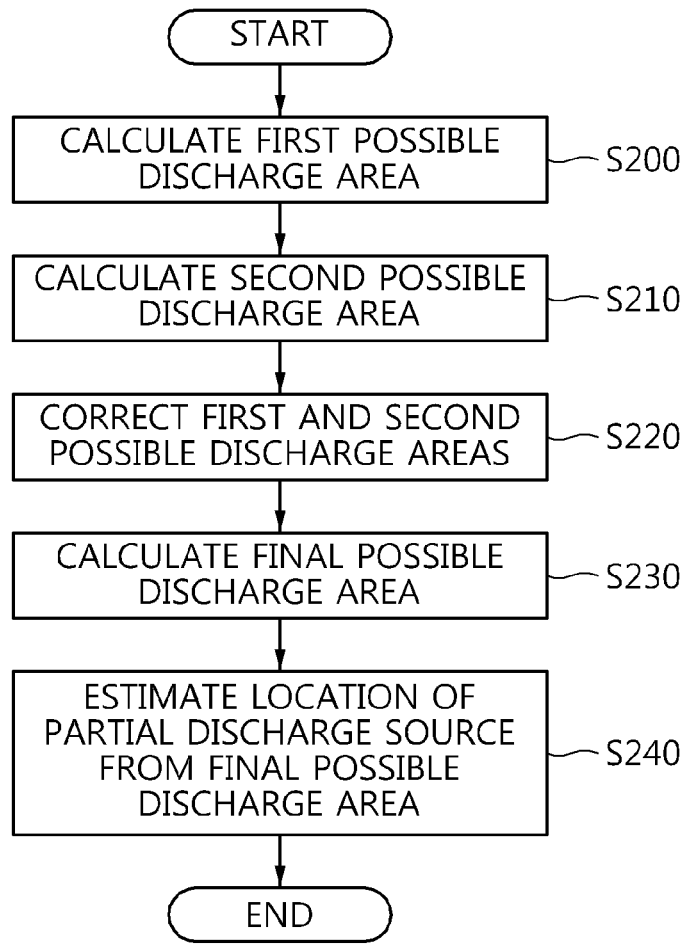
FIG. 11 is a diagram showing an embodiment of a transformer fault detection method according to the present invention.

FIG. 10 is a flowchart showing a transformer fault detection method according to the present invention. FIG. 11 is a flowchart showing an embodiment of the transformer fault detection method according to the present invention.

Referring to FIG. 10, the transformer fault detection method according to the present invention includes a first possible discharge area calculation step S100, a second possible discharge area calculation step S110, and a final possible discharge area calculation step S120. At step S100, a first possible discharge area estimated to be the location of the partial discharge source of the transformer is calculated based on the arrival times of signals sensed by different sensors located on an upper drain valve present in an upper portion of the transformer. At step S110, a second possible discharge area estimated to be the location of the partial discharge source of the transformer is calculated based on the arrival times of signals sensed by different sensors located on a lower drain valve present in a lower portion of the transformer. At step S120, a final possible discharge area estimated to be the location of the partial discharge source of the transformer is calculated based on an overlapping area between the first and second possible discharge areas.

An embodiment of the transformer fault detection method according to the present invention will be described in detail with reference to FIG. 11. At step S200, a first possible discharge area is calculated, and at step S210, a second possible discharge area is calculated. Thereafter, at step S220, the calculated first and second possible discharge areas are corrected. A detailed correction method is identical to that of the transformer fault detection apparatus according to the present invention.

Thereafter, at step S230, a final possible discharge area is calculated based on the corrected first and second possible discharge areas. At step S240, the location of the partial discharge source in the transformer is estimated from the calculated final possible discharge area, and then the transformer fault detection method of the present invention is terminated.

As described above, in accordance with the transformer fault detection apparatus and method according to the present invention, there is an advantage in that an abnormal signal such as a partial discharge signal in a transformer can be precisely and easily measured by installing sensors, which simultaneously measure an electromagnetic signal and an ultrasonic signal occurring in the transformer, on the drain valve of the transformer in order to detect a partial discharge and an arc occurring in the transformer. Further, the present invention is advantageous in that signals can be sensed using an integrated sensor unit installed on upper and lower drain valves present in the transformer, and the location of a partial discharge occurring in the transformer can be precisely estimated using a difference between the propagation velocity of an electromagnetic signal and the propagation velocity of an ultrasonic signal within the insulating oil.

As described above, in the transformer fault detection apparatus and method according to the present invention, the configurations and schemes in the above-described embodiments are not limitedly applied, and some or all of the above embodiments can be selectively combined and configured so that various modifications are possible.

What is claimed is:

1. A transformer fault detection apparatus, comprising:
an integrated sensor unit for sensing signals through a plurality of sensors located on each of an upper drain valve and a lower drain valve present in a transformer;
a first possible discharge area calculation unit for calculating a first possible discharge area estimated to be a location of a partial discharge source of the transformer, based on arrival times of signals sensed by different sensors located on the upper drain valve;
a second possible discharge area calculation unit for calculating a second possible discharge area estimated to be the location of the partial discharge source of the transformer, based on arrival times of signals sensed by different sensors located on the lower drain valve;
a final possible discharge area calculation unit for calculating a final possible discharge area estimated to be the location of the partial discharge source of the transformer, based on an overlapping area between the first possible discharge area and the second possible discharge area; and
a partial discharge source location estimation unit for estimating the location of the partial discharge source from the final possible discharge area, based on a difference between arrival times of an identical signal that has reached a sensor located on the upper drain valve and a sensor located on the lower drain valve,
wherein the first possible discharge area calculation unit calculates a three-dimensional (3D) first possible discharge area, based on a difference between arrival times of a first electromagnetic signal sensed by a first electromagnetic sensor located on the upper drain valve and a first ultrasonic signal sensed by a first ultrasonic sensor located on the upper drain valve,
wherein the second possible discharge area calculation unit calculates a 3D second possible discharge area, based on a difference between arrival times of a second electromagnetic signal sensed by a second electromagnetic sensor located on the lower drain valve and a second ultrasonic signal sensed by a second ultrasonic sensor located on the lower drain valve,
wherein the final possible discharge area calculation unit calculates a two-dimensional (2D) final possible discharge area generated by causing a point, at which the 3D first possible discharge area and the 3D second possible discharge area intersect each other, to be included in a circumference.

2. The transformer fault detection apparatus of claim 1, further comprising a possible discharge area correction unit for correcting the first possible discharge area and the second possible discharge area based on media of the signals.

3. The transformer fault detection apparatus of claim 1, wherein the integrated sensor unit comprises at least one ultrasonic sensor and at least one electromagnetic sensor, wherein the ultrasonic sensor and the electromagnetic sensor are integrally coupled to each other.

4. The transformer fault detection apparatus of claim 1, wherein the partial discharge source location estimation unit estimates the location of the partial discharge source from the final possible discharge area, based on a difference between arrival times of the first electromagnetic signal and the second electromagnetic signal.

5. The transformer fault detection apparatus of claim 4, wherein the integrated sensor unit further comprises a gas sensor located on the upper drain valve or the lower drain valve and configured to sense gas contained in insulating oil present in the transformer while being in direct contact with the insulating oil.

6. The transformer fault detection apparatus of claim 4, wherein the integrated sensor unit further comprises a temperature sensor located on the upper drain valve or the lower drain valve and configured to sense a temperature of the insulating oil present in the transformer.

7. A transformer fault detection method, comprising:
calculating, by a first possible discharge area calculation unit, a first possible discharge area estimated to be a location of a partial discharge source of a transformer, based on arrival times of signals sensed by different sensors located on an upper drain valve present in an upper portion of the transformer;
calculating, by a second possible discharge area calculation unit, a second possible discharge area estimated to be the location of the partial discharge source of the transformer, based on arrival times of signals sensed by different sensors located on a lower drain valve present in a lower portion of the transformer;
calculating, by a final possible discharge area calculation unit, a final possible discharge area estimated to be the location of the partial discharge source of the transformer, based on an overlapping area between the first possible discharge area and the second possible discharge area; and
after calculating the final possible discharge area, estimating the location of the partial discharge source from the final possible discharge area, based on a difference between arrival times of an identical signal that has reached a sensor located on the upper drain valve and a sensor located on the lower drain valve,
wherein calculating the first possible discharge area comprises calculating a three-dimensional (3D) first possible discharge area, based on a difference between arrival times of a first electromagnetic signal sensed by a first electromagnetic sensor located on the upper drain valve and a first ultrasonic signal sensed by a first ultrasonic sensor located on the upper drain valve,
wherein calculating the second possible discharge area comprises calculating a 3D second possible discharge area, based on a difference between arrival times of a second electromagnetic signal sensed by a second electromagnetic sensor located on the lower drain valve and a second ultrasonic signal sensed by a second ultrasonic sensor located on the lower drain valve,
wherein calculating the final possible discharge area comprises calculating a two-dimensional (2D) final possible discharge area generated by causing a point, at which the 3D first possible discharge area and the 3D second possible discharge area intersect each other, to be included in a circumference.

8. The transformer fault detection method of claim 7, further comprising correcting the first possible discharge area and the second possible discharge area based on media of the signals.

9. The transformer fault detection method of claim 7, wherein the upper drain valve and the lower drain valve are configured such that an ultrasonic sensor and an electromagnetic sensor are located on each of the upper drain valve and the lower drain valve, the ultrasonic sensor and the electromagnetic sensor being integrally coupled to each other.

10. The transformer fault detection method of claim 7, wherein estimating the location of the partial discharge source comprises estimating the location of the partial discharge source from the final possible discharge area, based on a difference between arrival times of the first electromagnetic signal and the second electromagnetic signal.

11. The transformer fault detection method of claim 10, further comprising sensing gas contained in insulating oil present in the transformer through a gas sensor located on the upper drain valve or the lower drain valve and configured to be in direct contact with the insulating oil.

12. The transformer fault detection method of claim 10, further comprising sensing a temperature of insulating oil present in the transformer through a temperature sensor located on the upper drain valve or the lower drain valve.

* * * * *